(12) United States Patent
Shibamoto et al.

(10) Patent No.: US 12,318,473 B2
(45) Date of Patent: Jun. 3, 2025

(54) COMPOSITION FOR CONTROLLING INDIGENOUS BACTERIAL FLORA IN THE SKIN

(71) Applicant: Shimadzu Corporation, Kyoto (JP)

(72) Inventors: Shigeaki Shibamoto, Kyoto (JP); Yasuko Yoneda, Kyoto (JP); Ryogo Takai, Kyoto (JP); Kohei Yamamoto, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 17/704,653

(22) Filed: Mar. 25, 2022

(65) Prior Publication Data

US 2022/0387298 A1 Dec. 8, 2022

(30) Foreign Application Priority Data

May 31, 2021 (JP) .................................. 2021-091151

(51) Int. Cl.
*A61K 8/98* (2006.01)
*A61Q 17/00* (2006.01)
*A61Q 19/00* (2006.01)

(52) U.S. Cl.
CPC ............ *A61K 8/987* (2013.01); *A61Q 17/005* (2013.01); *A61Q 19/007* (2013.01); *A61K 2800/805* (2013.01)

(58) Field of Classification Search
CPC .................................................... A61K 8/987
See application file for complete search history.

(56) References Cited

U.S. PATENT DOCUMENTS 5,405,608 A * 4/1995 Xu ........................ A61K 36/66
514/783

FOREIGN PATENT DOCUMENTS

| CN | 110540550 |   | 12/2019 |
| CN | 111281966 | A * | 6/2020 |
| JP | 58032825 | * | 2/1983 |
| JP | 2018-52891 |   | 4/2018 |

OTHER PUBLICATIONS

Pratiwi (A Study on Entrapment Efficiency of Earthworms (Lumbricus rubellus Extract in the Ethosomal Drug Delivery System) (Year: 2017).*
Higuera (What is Squalane and what are its benefits for skin and hair?) (Year: 2019).*
Ambavade et al. Pharmacological, Nutritional, and Analytical aspects of beta-sitosterol: A review (Year: 2014).*
DBpedia. About: Di Long (extract). Retrieved (Year: 2024).*
Fernandes et al. Phytosterols: Applicants and recovery methods. (Year: 2006).*
"Shiseido discovers that sensitive skin is low in skin microbiome diversity", issued Aug. 19, 2020, Shiseido Co., Ltd., Internet (URL: https://corp.shiseido.com/jp/news/detail.html?n=00000000002960), with English translation.
Machine English Translation of Office Action issued Mar. 19, 2024 in Chinese Patent Application No. 202210604406.5.
Notice of Reasons for Refusal issued Jul. 31, 2024 in Japanese Application No. 2021-091151, with English machine translation.
Yamamoto Kohei, Development of application of earthworm lipids as a material for reducing atopic dermatitis, JST Project Databases, Apr. 26, 2016, Internet:https://projectdb.jst.go.jp/grant/JST-PROJECT-12102304/>, with English machine translation.

* cited by examiner

*Primary Examiner* — Sarah Alawadi
(74) *Attorney, Agent, or Firm* — Wenderoth, Lind & Ponack, L.L.P.

(57) ABSTRACT

The present invention chiefly aims to provide a novel composition for controlling indigenous bacterial flora in the skin which can enhance or improve the diversity of bacterial species in the indigenous bacterial flora in the skin relative to the condition before treatment. The present invention can include, for example, a composition (e.g., an ointment, a liquid) for controlling the diversity of bacterial species in indigenous bacterial flora in the skin, comprising an effective amount of earthworm lipids extracted from a raw earthworm (*Lumbricus rubellus*), and a base. The composition of the present invention is useful, for example, as a raw material for skin care products and cosmetics.

12 Claims, 3 Drawing Sheets

COMPOSITION FOR CONTROLLING INDIGENOUS BACTERIAL FLORA IN THE SKIN

TECHNICAL FIELD

The present invention relates to a composition for controlling indigenous bacterial flora in the skin, which mainly pertains to the technical field of skin care. Specifically, the present invention relates to a composition for controlling indigenous bacterial flora in the skin containing what is called earthworm lipids extracted from earthworms.

BACKGROUND OF THE INVENTION

In addition to the functions of epidermis and stratum corneum to separate the body from the outside, the formation of sebaceous membranes plays an important role in the skin barrier mechanism of humans. The sebaceous membrane is formed with sodium fatty acids, which is produced by the degradation of sebum secreted from sebaceous glands into free fatty acids by the enzyme lipase derived from microorganisms in the skin, and then the binding of the free fatty acids to sodium contained in sweat secreted from sweat glands. The sebaceous membrane serves as a physical barrier to prevent invasion of foreign substances, and also has functions to prevent dryness of the skin by suppressing moisture transpiration from the epidermis, as well as to stabilize the environment of the skin surface. Poor amount of sebum secretion, or poor amount of perspiration even in the sufficient amount of sebum secretion would make it hard to form the sodium fatty acids, and would lower the barrier effect due to an insufficient formation of the sebaceous membrane.

On the skin surface, usually over 200 species of microorganisms adapted to the environment thereof form a flora while keeping a balance, and prevents the proliferation of pathogenic bacteria. Some of the free fatty acid isomers produced when the sebum is degraded by lipase of skin microorganisms are effective in suppressing the proliferation of certain types of bacteria, and the abundance ratio of the constituent fatty acids seems to affect the microbial flora in the skin. It is considered that resistance to pathogenic microorganisms differs depending on the composition of the microbial flora in the skin.

Thus, controlling the composition or the diversity of microbial flora or indigenous bacterial flora in the skin to the same conditions as healthy skin is important for maintaining healthy skin, preventing the invasion of pathogenic microorganisms, and inhibiting inflammation such as atopic dermatitis. Non-Patent Document 1 introduces that the diversity of indigenous bacterial flora in the skin is low in the sensitive skin.

A coating agent for controlling indigenous bacteria in the skin comprising magnesium lactate and/or calcium lactate as an active ingredient is known as a technique for controlling indigenous bacterial flora in the skin, for example (see Patent Document 1). According to Patent Document 1, the coating agent for controlling the indigenous bacteria in the skin could reduce the number of bad bacteria of the indigenous bacteria in the skin, while suppressing the reduction of the number of good bacteria.

On the other hand, with regard to earthworms, particularly cultivated red earthworms (*Lumbricus rubellus*), those that have been dried and processed into powder form are widely distributed as supplements or pharmaceuticals. The earthworms contain components that have antipyretic and analgesic effects, as well as the enzyme lumbrokinase, which is considered to have the effect of lysing thrombi.

PRIOR ART DOCUMENTS

Patent Document

Patent Document 1: JP, 2018-52891, A

Non-Patent Document

Non-Patent Document 1: "Shiseido discovers that sensitive skin is low in skin microbiome diversity." issued on 19 Aug. 2020: Shiseido Co., Ltd., Internet (URL: https://corp.shiseido.com/jp/news/detail.html?n=00000000002960)

SUMMARY OF THE INVENTION

Problem to be Solved by the Invention

As described above, controlling the composition or the diversity of indigenous bacterial flora in the skin to the same condition as healthy skin is important for maintaining healthy skin, preventing the invasion of pathogenic microorganisms, and suppressing inflammation such as atopic dermatitis.

The present invention chiefly aims to provide a novel composition for controlling indigenous bacterial flora in the skin which can enhance or improve the diversity of bacterial species in the indigenous bacterial flora in the skin (the diversity of microorganisms on the skin surface) relative to the condition before treatment.

Means for Solving the Problems

The present inventors have found after intensive studies that earthworm lipids extracted from earthworms have an effect of enhancing the diversity of indigenous bacteria in the skin, and the like, and the present invention was completed.

The present invention can include, for example, the following embodiments.

[1] A composition used for controlling a degree of the diversity of bacterial species in indigenous bacterial flora in the skin, comprising an effective amount of earthworm lipids and a base.

[2] The composition according to [1] mentioned above, wherein the earthworm lipids are obtained from an extraction residue after extracting and removing proteins from a raw earthworm.

[3] The composition according to [1] or [2] mentioned above, wherein the earthworm is a red earthworm (*Lumbricus rubellus*).

[4] The composition according to any one of [1] to [3] mentioned above, which is directed for application to a subject with low sebum secretion or a subject with symptom of atopic dermatitis on the skin.

[5] An enhancer of monoene fatty acid having 16 carbon atoms on the skin, comprising the composition according to any one of [1] to [4] mentioned above.

[6] The composition according to any one of [1] to [4] mentioned above, or the enhancer of monoene fatty acid having 16 carbon atoms on the skin according to [5] mentioned above, wherein the dosage form is an ointment, a cream, a gel, a liquid, a cataplasm, a tape, a sheet, an aerosol, an external powder, a spray, or a bathing agent.

[7] A cosmetic, comprising the composition or the enhancer of monoene fatty acid having 16 carbon atoms on the skin according to any one of [1] to [6] mentioned above.

[8] A composition for controlling indigenous bacterial flora in the skin, which is obtained by extracting from an extraction residue after proteins are extracted and removed from a raw earthworm, that is an earthworm dehydrated cake, using a polar organic solvent, or by saponification of the earthworm dehydrated cake with an alkali followed by extraction from the saponified product using a nonpolar organic solvent.

[9] An earthworm lipid for controlling indigenous bacterial flora in the skin, which is obtained by extracting from an extraction residue after proteins are extracted and removed from a raw earthworm, that is an earthworm dehydrated cake, using a polar organic solvent, or by saponification of the earthworm dehydrated cake with an alkali followed by extraction from the saponified material using a nonpolar organic solvent.

[10] The composition for controlling indigenous bacterial flora in the skin according to [8] mentioned above or the earthworm lipid for controlling indigenous bacterial flora in the skin according to [9] mentioned above, wherein the polar organic solvent is a mixed solvent of a chlorine-based organic solvent and an alcohol-based organic solvent.

[11] The composition for controlling indigenous bacterial flora in the skin according to [8] mentioned above or the earthworm lipid for controlling indigenous bacterial flora in the skin according to [9] mentioned above, wherein the nonpolar organic solvent is a hydrocarbon-based organic solvent.

[12] A method of producing a composition for controlling the diversity of bacterial species in indigenous bacterial flora in the skin, comprising a step of extracting earthworm lipids from an earthworm and a step of mixing the earthworm lipids with a base.

Effect of the Invention

The present invention enables the diversity of microorganisms on the skin or the diversity of indigenous bacteria in the skin to be enhanced or improved relative to the condition before application, thereby enhancing the barrier function of the skin and suppressing the proliferation of the pathogenic bacteria.

EMBODIMENT FOR CARRYING OUT THE PRESENT INVENTION

Figure 1:
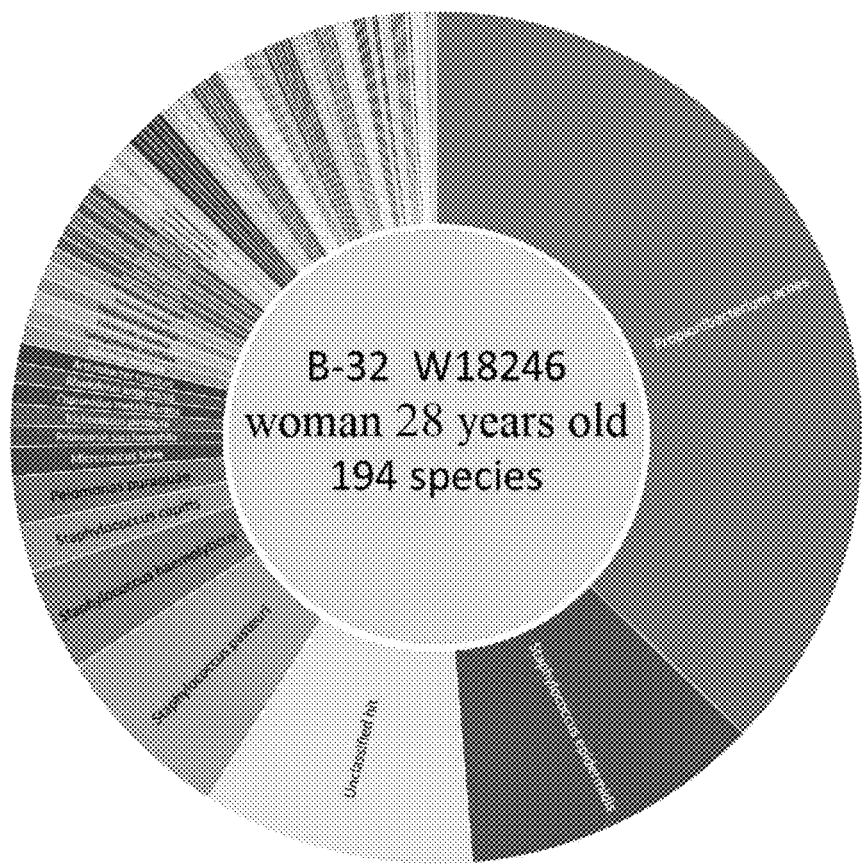
FIG. 1 represents indigenous bacterial flora in the skin. The upper figure shows the results of healthy persons, and the lower figure shows the results of those who have atopic dermatitis.
Figure 1:
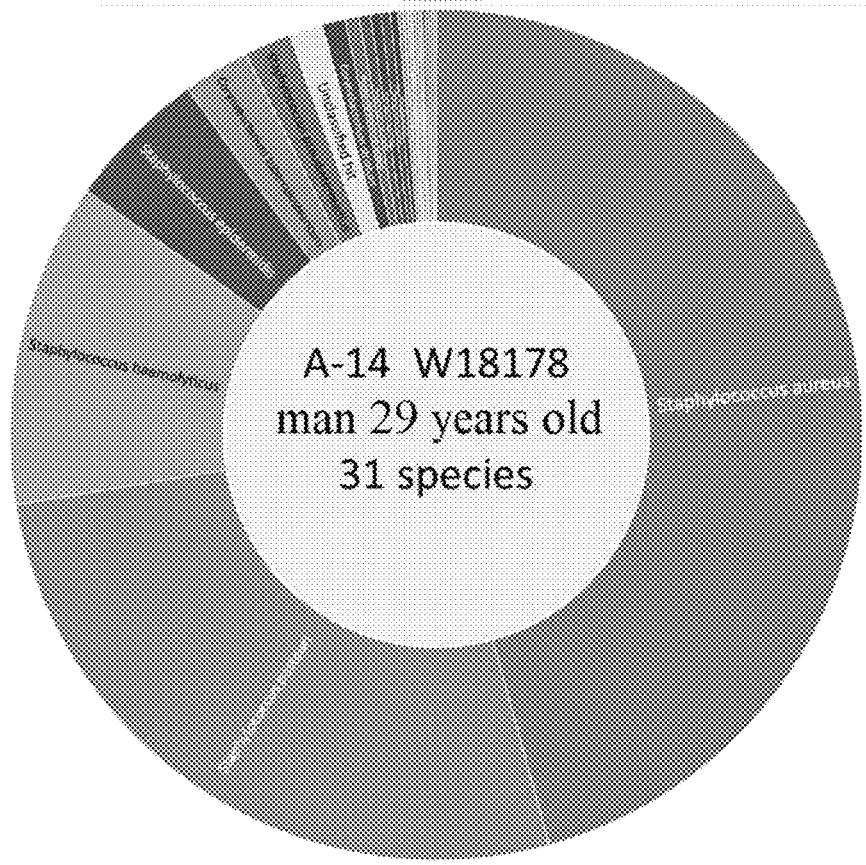

Hereinafter, the embodiment of the present invention will be described in detail.

1 Composition According to the Embodiment of the Present Invention

A composition according to the embodiment of the present invention (hereinafter, referred to as "the composition of the present invention") is a composition for controlling the diversity of bacterial species of indigenous bacterial flora in the skin, that is the diversity of microorganisms on the skin or the diversity of indigenous bacteria in the skin, comprising an effective amount of earthworm lipids. The composition of the present invention may be preferably used to enhance or improve the diversity of bacterial species in indigenous bacterial flora in the skin relative to the pre-application condition or to maintain the diversity.

Here, the term "controlling" refers to varying or maintaining the number of species in indigenous bacterial flora in the skin or the occupancies for a plurality of species in the flora, i.e., the control of indigenous bacterial flora in the skin, and includes enhancing or improving the diversity of species in indigenous bacterial flora in the skin, i.e., the improvement of indigenous bacterial flora in the skin, compared to the condition prior to application of the composition of the present invention, and maintaining the diversity that is already at a high level due to improvement of indigenous bacterial flora in the skin or other factors, i.e., the maintenance of indigenous bacterial flora in the skin. The term "diversity" refers to a concept that combines the aspect of the abundance of bacterial species, i.e., the number of species of bacterium, and the aspect of the uniformity of bacterial species, i.e., the smallness of variation in the number of individuals among bacterial species. The greater the number of bacterial species is, and further the greater the similarity in population size is among bacterial species, or the smaller the occupancy bias is, it can be said that the diversity is greater or better. Considering the above two aspects, the existence or degree of improvement can be judged using as an index, for example, the diversity index of Simpson or Simpson's Index, Shannon Entropy, and the RI index of Nakamura (Nakamura, Bulletin of Setouchi Junior College, No. 24: 37-41, 1994). The term "effective amount" refers to an amount by which the effect of the said control such as the improvement of indigenous bacterial flora in the skin and the maintenance of indigenous bacterial flora in the skin is confirmed by those skilled in the art.

The term "earthworm lipid" refers to a wide variety of lipid groups contained in earthworms, especially a wide variety of lipid groups contained in all parts of earthworms. The lipid groups are generally comprised of 100 or more various lipids. For example, the earthworm lipids can be obtained as an extract by performing an extraction operation for obtaining a lipid using a polar organic solvent from an extraction residue or an earthworm dehydrated cake of a raw earthworm from which proteins have been extracted and removed. The polar organic solvent includes, for example, a mixed organic solvent of a chlorine-based organic solvent and an alcohol-based organic solvent, and specifically include a mixed organic solvent of chloroform and methanol, or a mixed organic solvent obtained by adding water thereto. Moreover, the earthworm lipids can be obtained by saponifying an earthworm dehydrated cake with an alkali, making the alkaline solution of a saponified product acidic, and then extracting the earthworm lipids from the acidic solution with a non-polar organic solvent. The non-polar organic solvent includes, for example, a hydrocarbon-based organic solvent, and specifically includes hexane, cyclohexane, and heptane.

The resulting earthworm lipids, that is the total lipids, may be oily or solid state.

The obtained extract may be added with an additive and properly processed into a composition, which is solid, semi-solid, liquid, or the like, containing the extract.

Earthworms relating to the present invention are not particularly limited, and genus *Lumbricus* is preferred, and *Lumbricus rubellus*, namely what is called a red earthworm is more preferred.

The dosage form of the composition of the present invention is not particularly limited, as long as it can be applied directly to the surface of the skin, and can include, for example, an ointment; a cream; a gel; a liquid (e.g., a suspension, an emulsion, a lotion, and the like); a cataplasm; a tape; a sheet; an aerosol; an external powder; a spray; and a bathing agent.

In preparing these preparations, in addition to the earthworm lipids, various formulating ingredients can be appropriately selected and used to an inert base or a carrier which is used in preparing a conventional external preparation. Such a base or ingredients can include, in the case of an ointment, a gel, or a lotion, a base such as white vaseline, yellow vaseline, lanolin, white beeswax, cetanol, stearyl alcohol, stearic acid, hardened oil, gelled hydrocarbons, polyethylene glycol or macrogol, 1,3-butylene glycol, ethanol, isopropanol, liquid paraffin, squalene and the like; solvents and solubilizing agents such as oleic acid, isopropyl myristate, glycerin triisooctane, crotamiton, diethyl sebacate, diisopropyl adipate, hexyl laurate, fatty acid, fatty acid esters, aliphatic alcohols, vegetable oils, and the like; antioxidants such as thimole, tocopherol derivatives, ascorbic acid, dibutylhydroxytoluene, butylhydroxyanisole, and the like; antiseptics such as phenoxyethanol, parahydroxybenzoate esters and the like; moisturizing agents such as glycerin, monostearate glycerin, propylene glycol, sodium hyaluronate, and the like; surfactants such as polyoxyethylene derivatives, glycerine fatty acid esters, sucrose fatty acid esters, sorbitan fatty acid esters, propylene glycol fatty acid esters, lecithin, and the like; thickening agents such as carboxyvinyl polymers, xanthan gum, carboxymethylcellulose, carboxymethylcellulose sodium salts, hydroxypropylcellulose, hydroxypropylmethylcellulose, and the like; stabilizers such as sodium edetate hydrate, citric acid hydrate, sodium citrate hydrate, and the like, which include chelating agents, and antioxidants; silicones such as dimethicon, cyclic silicone, modified silicone and the like; and keratin softening components such as salicylic acid and the like. In addition, preservatives, absorption accelerators, pH adjusting agents, colorants, which include pigments such as iron oxide, flavoring agents, ultraviolet absorbers, ultraviolet scattering agents (e.g., titanium oxide, zinc oxide, and the like), excipients, dispersants, emulsifiers, isotonic agents, buffering agents, fillers, crosslinking agents, refreshing agents, coating agents, and other suitable additives can be formulated as desired.

For the cataplasm, tackifiers such as polyacrylic acid, polyacrylic acid copolymer, and the like; crosslinking agents such as aluminum sulfate, aluminum potassium sulfate, aluminum chloride, magnesium aluminometasilicate, dihydroxyaluminum acetate, and the like; thickening agents such as polyacrylic acid sodium, polyvinyl alcohol, polyvinyl pyrrolidone, gelatin, sodium alginate, carboxymethyl cellulose, carboxymethylcellulose sodium salts, hydroxypropyl cellulose, hydroxypropylmethylcellulose, and the like; polyhydric alcohols such as glycerin, polyethylene glycol or macrogol, propylene glyco1,3-butanediol, and the like; surfactants such as polyoxyethylene derivatives and the like; perfumes such as L-menthol and the like; antiseptics such as parahydroxybenzoic acid esters and the like; purified water; and supporters such as plastic films, nonwoven fabrics, cottons and the like can be formulated. In addition, stabilizers, preservatives, absorption promotors, pH adjusting agents, and other suitable additives can be formulated as desired.

For the tape, adhesives such as natural rubber, isoprene rubber, polyisobutylene, polybutene, liquid polyisoprene, styrene-isoprene-styrene block copolymer, that is SIS block copolymer, styrene-butadiene-styrene block copolymer, styrene-ethylene-butylene-styrene block copolymer, acrylic resins such as (meta) acrylic alkyl ester (co)polymer, polyacrylic ester, and methacrylic ester, and the like; tackifier resins such as alicyclic saturated hydrocarbon-based resin, rosin-based resin, and terpene-based resin, and the like; softening agents such as liquid rubber, liquid paraffin, and the like; antioxidants such as dibutyl hydroxytoluene, and the like; polyhydric alcohols such as propylene glycol, and the like; absorption accelerators such as oleic acid, and the like; surfactants such as polyoxyethylene derivatives, and the like; and other suitable additives can be formulated. Moreover, it is also possible to prepare a water-containing tape agent by adding water-containable polymers such as sodium polyacrylate and polyvinyl alcohol, and a small amount of purified water. Even in this case, stabilizers, preservatives, absorption promotors, pH adjusting agents, and other suitable additives can be additionally formulated as desired.

For the aerosol, bases such as white vaseline, yellow vaseline, lanolin, white beeswax, cetanol, stearyl alcohol, stearic acid, hardened oil, gelled hydrocarbons, polyethylene glycol or macrogol, liquid paraffin, squalane, and the like, which are used for the preparation of an ointment, a cream, a gel, a liquid (e.g., a suspension, an emulsion, and a lotion); solvents and solubilizing agents such as oleic acid, isopropyl myristate, diisopropyl adipate, isopropyl sebacate, glycerin triisooctane, crotamiton, diethyl sebacate, hexyl laurate, fatty acid, fatty acid esters, aliphatic alcohols, vegetable oils, and the like; antioxidants such as tocopherol derivatives, ascorbic acid, dibutylhydroxytoluene, butylhydroxyanisole, and the like; antiseptics such as parahydroxybenzoate esters, and the like; moisturizing agents such as glycerin, propylene glycol, sodium hyallonate, and the like; surfactants such as polyoxyethylene derivatives, glycerine fatty acid esters, sucrose fatty acid esters, sorbitan fatty acid esters, propylene glycol fatty acid esters, lecithin, and the like; thickening agents such as carboxyvinyl polymers, xanthan gum, carboxymethylcellulose, carboxymethylcellulose sodium salts, hydroxypropylcellulose, hydroxypropylmethylcellulose, and the like; propellants such as dimethyl ether, liquefied petroleum gas, fluorohydrocarbons, and the like; compressed gases such as carbon dioxide, nitrogen, nitrous oxide, and the like; and in addition, various stabilizers, buffers, corrigents, suspending agents, emulsifying agents, flavoring agents, preservatives, solubilizing agents, and other suitable additives, can be formulated.

For the external powder, excipients such as potato starch, rice starch, corn starch, talc, zinc oxide, and the like, and other suitable additives can be formulated. Even in this case, various stabilizers, preservatives, absorption promotors, saccharides such as lactose and the like, and other suitable additives can be additionally formulated as desired.

The method of preparing the above-mentioned external preparation is not particularly limited, and the preparation can be produced by a conventional method such as kneading well suitable components and a suitable base component depending on a desired dosage form. Moreover, the preparation of a cataplasm or a tape can be performed by spreading and drying the kneaded mixture on a release paper, followed by sticking to a flexible supporter, and then cutting into a desired size.

The above-mentioned external preparation can be used by a conventional method such as applying directly to the skin, or applying to the skin through coating on or impregnating into a fabric or other supporters, for an ointment; a cream; a gel; a liquid (e.g., a suspension, an emulsion, a lotion, and the like); an aerosol, and an external powder, for example. Moreover, for a cataplasm or a tape, it can be used by applying directly to the skin, for example.

2 Use, Producing Process, Etc. Of the Composition of the Present Invention

The composition of the present invention can be used to enhance or improve the diversity of indigenous bacteria in the skin relative to the condition before application. Moreover, since the composition of the present invention can increase the ratio of the monoene fatty acid having 16 carbon atoms, which would have high antibacterial activity, relative to before application, the composition of the present invention can also be used as an enhancer for increasing the ratio of the monoene fatty acid having 16 carbon atoms on the skin (hereinafter, referred to as "the monoene enhancer of the present invention").

The composition of the present invention or the monoene enhancer of the present invention is, as is apparent from the experimental results described later, highly effective for a subject having a low sebum secretion or a symptom of atopic dermatitis, and therefore, it is preferable to apply the composition of the present invention to these subjects. Here, "low sebum secretion" means that the amount of sebum secretion is generally no more than, for example, half, one-third, one-fifth, or one-tenth of the average sebum secretion of healthy people, although varying depending on sex, age, and the like.

The composition of the present invention can be produced, for example, by adding other components such as excipients, additives, and the like to an earthworm lipid within a range not impairing the effect of the present invention, followed by mixing or the like by a conventional method. It is also possible to produce the composition of the present invention according to the method for producing each of the above-mentioned preparations.

The earthworm lipids can be prepared, for example, by performing an extraction operation to obtain lipids using an organic solvent from extraction residues or earthworm dehydrated cakes after the proteins are extracted and removed from a raw earthworm by a conventional method, e.g., enzymatic degradation, insolubilization by addition of acid or organic solvent, insolubilization by heating, or cooling, or physical removal by ultrafiltration, dialysis, or centrifugation. The preparation can also be performed by saponifying the earthworm dehydrated cakes with an alkali, making the alkaline solution of the saponified product acidic, and then extracting the earthworm lipids with an organic solvent. Note that the earthworm dehydrated cakes are known and can be obtained from a manufacturer who extracts proteins from raw earthworms.

Specific methods for obtaining lipids from the earthworm dehydrated cakes can include, for example, Bligh-Dyer method, Folch method, and a direct saponification method. The total lipids of earthworms can be obtained by these methods.

In the case of Bligh-Dyer method or the Folch method, the earthworm lipid can be obtained by extracting from, for example, an earthworm dehydrated cake using a polar organic solvent as an extraction solvent. The polar organic solvent can include, for example, a mixed organic solvent of a chlorine-based organic solvent and an alcohol-based organic solvent, and specifically include a mixed solvent of chloroform and methanol, or a mixed solvent of chloroform, methanol and water. When a mixed solvent of chloroform and methanol is used as an extraction solvent, the mixing ratio of chloroform and methanol is appropriately selected, and is suitably within a range of 1:3 to 3:1 by volume, and preferably within a range of 1:2 to 2:1.

In the case of a direct saponification method, the earthworm lipids can be obtained by saponifying, for example, a fatty acid ester in an earthworm dehydrated cake with an alkali and extracting the fatty acid from the saponified product with a nonpolar organic solvent. The nonpolar organic solvent can include, for example, a hydrocarbon-based organic solvent, and specifically include hexane, cyclohexane, and heptane.

The total lipids obtained as described above usually contains a highly unsaturated fatty acid and this acid is easy to oxidize, and in consideration of the irritancy of the oxide to the skin, the total lipids may be purified by a conventional method such as using a silica gel column for removing a highly unsaturated fatty acid. Instead of removing a highly unsaturated fatty acid, it is also possible to cope with the irritation to the skin by using an antioxidant.

The earthworm lipids or the total lipids obtained by the above extraction operation or the like is usually an extract in oily form. A composition, which is in solid, semi-solid, liquid, or the like, obtained by adding an additive to the extract followed by a proper processing may be used as earthworm lipids.

The composition of the present invention or the monoene enhancer of the present invention can also be used as a raw material for a cosmetic. The cosmetic containing the composition of the present invention or the monoene enhancer of the present invention (hereinafter, referred to as "the cosmetic of the present invention") can be referred to as a functional cosmetic capable of enhancing or improving the diversity of indigenous bacteria in the skin from the condition before application, or a functional cosmetic capable of increasing the proportion of the monoene fatty acid having 16 carbon atoms on the skin relative to the condition before application. Moreover, the cosmetic of the present invention is not limited to a functional cosmetic, and may be, for example, a skin care cosmetic, a skin-beautifying cosmetic, or a body care cosmetic.

The cosmetic of the present invention may be, for example, in transparent liquid, dispersed liquid, milky, creamy, gel-like, semi-solid, solid, foam-like, powdery, granular, aerosol-like, or sheet-like form.

Here, the term "cosmetic" includes not only "cosmetics" as defined in the Pharmaceutical and Medical Device Act, but also "quasi-drugs" such as medicated cosmetics.

In producing the cosmetic of the present invention, various formulating ingredients may be appropriately selected and used in addition to the composition of the present invention and the monoene enhancer of the present invention. The formulating ingredients can include water (e.g., purified water, distilled water, ion-exchanged water, and the like); monohydric alcohols (e.g., ethanol, isopropanol, and the like); moisturizers; oil agents; surfactants; dyes and colors; flavoring agents; active whitening ingredients; anti-wrinkle ingredients; ultraviolet absorbers; anti-fading agents; antioxidants; beauty ingredients; antiseptics; anti-inflammatory ingredients; sterilizing ingredients; antipruritic ingredients; and the like.

The above-mentioned moisturizers can include, for example, polyhydric alcohols such as glycerin, propylene glycol, dipropylene glycol, 1,3-butylene glycol, polyethylene glycol (300, 400, 1500, and 4000), polyglycerin, and the like; saccharides such as glucose, sucrose, trehalose, pullulan, maltitol, and the like; amino acids such as pyrrolidone carboxylic acid, citrulline, and the like; polysaccharides such as heparin analogs, mucopolysaccharides, and the like; biopolymers such as hyaluronic acid or salts thereof, collagen, and the like.

The above-mentioned oil agents can include, for example, fats and oils such as cacao oil, shea oil, olive oil, camellia oil, macadamia nut oil, almond oil, coconut oil, sesame oil, corn oil, soybean oil, safflower oil, horse oil, egg yolk oil, mink oil, beef tallow, horse fat, and the like; waxes such as carnauba wax, candelilla wax, jojoba oil, beeswax, lanolin, orange roughly oil, and the like; fatty acids such as lauric acid, myristic acid, palmitic acid, palmitoleic acid, stearic acid, oleic acid, linoleic acid, linolenic acid, and the like; higher alcohol such as cetanol, stearyl alcohol, isostearyl alcohol, oleyl alcohol, lauryl alcohol, cholesterol, sitosterol, and the like; hydrocarbons such as liquid paraffin, vaseline, paraffin, ceresin, microcrystalline wax, squalane, pristane, and the like; esters such as glyceryl triisostearate, cetyl octarate, isopropyl myristate, cetyl lactate, diisostearyl malate, and the like; silicone oils such as siloxane, dimethicone, cyclic dime thylsilicone oil, methyl polysiloxate, methylphenyl polysiloxylate, and the like; and regardless of the origins such as animal oils, vegetable oils, synthetic oils, or the like, as well as the forms such as solid, liquid, volatile oils, and the like, others including hydrocarbons, oils and fats, waxes, hardened oils, ester oils, fatty acids, higher alcohols, silicone oils, lanoline derivatives, oily gelling agents, oil-soluble resins, and the like.

The above-mentioned surfactants can include, for example, anionic surfactants such as higher fatty acid soap, alkyl sulfate ester salt, alkyl ether sulfate ester salt, alkyl phosphate ester salt, alkyl ether phosphate ester salt, N-acyl amino acid salt, N-acyl-N-methyl taurine salt, and the like; cationic surfactants such as alkyl trimethylammonium chloride, dialkyl dimethylammonium chloride, benzalkonium chloride, and the like; amphoteric surfactants such as alkyldimethylaminoacetic acid betaine, alkylimidazolinium betaine, and the like; nonionic surfactants such as polyethylene glycol-type nonionic surfactants (e.g., polyethylene glycol alkyl ether, polyethylene glycol fatty acid ester, polyethylene glycol sorbitan fatty acid ester, and the like), polyhydric alcohol ester-type nonionic surfactant (e.g., glycerol fatty acid ester, polyglycerol fatty acid ester, sorbitan fatty acid ester, sucrose fatty acid ester, and the like), block polymer-type surfactants, and the like; polymeric surfactants such as acrylic acid-alkyl methacrylate (C10-30) copolymers, polyvinyl alcohols, sodium alginate, cellulose derivatives, and the like; natural surfactants such as lecithin and the like; and silicone surfactants.

The above-mentioned dyes and colors can include, for example, ultraviolet absorbers such as para-aminobenzoic acid derivatives, benzophenone derivatives, methoxy cinnamic acid derivatives, salicylic acid derivatives, and the like; ultraviolet scatterers such as titanium oxide fine particles, zinc dioxide fine particles, and the like; white pigments such as titanium dioxide, zinc oxide, and the like; colored pigments such as iron oxide, chromium oxide, carbon black, ultramarine blue, and the like; somatic pigments such as mica, sericite, talc, kaolin, and the like; pearlescent pigment; organic synthetic coloring matters such as azo-based dyes, xanthene-based dyes, indigoid-based dyes, lakes, azo-based pigments, phthalocyanine-based pigments, and the like; natural coloring matters such as (β-carotene, lycopene, crocin, raphanin, shisonin, carthamin, safflower yellow, chlorophyll, riboflavin, cochineal, alizarin, shikonin, curcumin, and the like; and polymer powders such as polyethylene powder, nylon powder, and the like.

The above-mentioned flavoring agents can include, for example, natural flavoring agents such as rose oil, jasmine oil, lavender oil, eucalyptus oil, patchouli oil, peppermint oil, lemon grass oil, lemon oil, lime oil, bergamot oil, sandalwood, cinnamon, bark oil, oakmoss, iris oil, vetiver oil, musk, civet, castoreum, ambergris, and the like; synthetic flavoring agents such as α-limonene, β-caryophyllene, cis-3-hexenol, linalool, farnesol, β-phenylethyl alcohol, 2,6-nonadienal, citral, α-hexyl cinnamic aldehyde, β-ionone, L-carvone, cyclopentadecanone, linalyl acetate, benzyl benzoate, γ-undecalactone, eugenol, rose oxide, phenylacetaldehyde dimethyl acetal, and the like.

The above-mentioned active whitening ingredients can include, for example, ascorbic acid phosphate ester magnesium salt, ascorbic acid-2-glucoside, 3-0-ethyl ascorbic acid, ascorbyl tetrahexyldecanoate, kojic acid, hydroquinone β-D-glucoside, ellagic acid, 4n-butylresorcinol, potassium 4-methoxysalicylate, 4-(4-hydroxyphenyl)-2-butanol, 5,5'-dipropylbiphenyl-2,2'-diol, linoleic acid, trans-4-aminomethylcyclohexanoic acid, cetyl tranexamate hydrochloride, chamomilla recutita extract, adenosine-1-phosphate-2Na, and nicotinamide.

The above-mentioned anti-wrinkle ingredients can include, for example, polyhydric alcohols such as glycerin, polyethylene glycol, propylene glycol, 1,3-butylene glycol, and the like; ceramides; amino acids such as serine, glycine, pyrrolidone carboxylic acid, and the like; collagen; hyaluronic acid; retinal or vitamin A; niacinamide; elastin; and proteoglycan.

The method for producing the cosmetic of the present invention is not particularly limited, and can be produced by a conventional method depending on the desired dosage form. It is possible to obtain a desired dosage form, for example, by mixing the above-mentioned various formulating ingredients including an earthworm lipid in accordance with the present invention by means of an emulsifier such as a batch type vacuum emulsifier, a disperser such as a colloid mill, or a mixer/pulverizer such as a hensil mixer or a hammer mixer, and then using a cooler, a molding machine, or the like as necessary.

Moreover, the cosmetic of the present invention obtained by an appropriate producing method can be processed to a cosmetic product by packaging in a tube container, a bottle container (narrow-mouthed), a cream container (wide-mouthed), a powder container, a compact container, a stick container, a pencil container, a container with a brush, a pumped bottle, an aerosol container, or the like, using, for example, a filling machine, a packaging machine or the like.

EXAMPLE

Hereinafter, the present invention will be illustrated in more detail with reference to Examples, but the present invention is not limited to the following Examples.

Reference Example: Examination of Diversity of Indigenous Bacteria in the Skin

For a total of 100 persons, 50 healthy persons (9 persons have a history of atopic dermatitis in the past) and 50 persons who have atopic dermatitis, the indigenous bacteria in the skin of each person were sampled, and the diversity of the bacteria species in the indigenous bacterial flora in the skin (diversity of indigenous bacteria in the skin) was investigated by metagenome analysis. The diversity was evaluated using Simpson's Diversity Index (D: Simpson's Index) and Shannon's Entropy (H: Shannon Entropy). The values of D and H were determined by the following equations, where pi (|pi|<1) is the ratio of the number of individuals in a species with the i-th greatest population size among the whole species in the skin indigenous flora against the total number of individuals in the flora.

$$D = 1 - \sum_i p_i^2 \quad \text{[Formula 1]}$$

$$H = -\sum_i p_i \ln p_i \quad \text{[Formula 2]}$$

Simpson's diversity index ranges from 0 to 1, and the closer to 1 the index is, the more uniformly diverse bacteria are present. In Shannon entropy, it can be found that the larger the absolute value of the numerical value is, the higher the diversity is. The analysis results are shown in Table 1 below.

TABLE 1

| | Symptoms of Atopic Dermatitis | | |
|---|---|---|---|
| Diversity Analysis | Holder group (50 persons) | Holder group in the past (9 persons) | Non-holder group (41 persons) |
| Simpson's Index | 0.81 | 0.81 | 0.84 |
| Shannon Entropy | 4.58 | 5.04 | 5.27* |

*p < 0.01

As shown in Table 1, it is clear that indigenous bacteria in the skin of the group without symptoms of atopic dermatitis is significantly more diverse (more bacterial species) than that of the group with symptoms of atopic dermatitis.

Although presented is one example for each, FIG. 1 shows a comparison between the indigenous bacterial flora in the skin of healthy persons and that of persons who have atopic dermatitis. In FIG. 1, the bacterial flora with 0.05% or more of occupancy is shown. As shown in FIG. 1, 194 species of bacterial flora were observed in healthy persons, and about ⅓ of the species were non-pathogenic acne bacteria, whereas only 31 species of bacterial flora were observed in persons who have atopic dermatitis, and not less than ⅓ of the species were pathogenic *Staphylococcus aureus*.

As the results of sebum sampling carried out at the same time as sampling of indigenous flora in the skin, the amount of sebum secretion in 23 out of 50 atopy holders was from a fraction to a tenth of that of healthy persons.

As described above, those who have atopic dermatitis tended to have a low diversity of indigenous bacteria in the skin, and a certain proportion of them tended to have not only a low diversity of indigenous bacteria in skin but also a low secretion of sebum.

Example 1: Preparation of Earthworm Lipid (1) Acquisition of Earthworm Materials The earthworm material for obtaining earthworm lipids used in the experiments described later was an extraction residue, i.e., earthworm dehydrated cake after extraction of protein from *Lumbricus rubellus* (red earthworm), and was supplied from Miyazaki Ketsuryu Institute in Miyazaki Prefecture.

(2) Preparation of the Earthworm Lipid

The earthworm lipids, that is the total lipids, were prepared by either of the following methods:

(2-1) Preparation by Bligh-Dyer Method

The total lipids were extracted from 10 g of earthworm dehydrated cake using 30 mL of a mixed solvent of chloroform and methanol (2:1). The earthworm lipids of approximately 2% were obtained.

(2-2) Preparation by Direct Saponification Method 60 g of earthworm dehydrated cake was collected in an eggplant-type flask, and 120 mL of 1 mol/KOH/ethanol was added, and then heated at 80° C. for 1 hours to saponify the fatty acid esters in the sample. After cooling, purified water was added, and the ethanol solution after saponification was filtered into a liquid extraction apparatus, followed by refluxing with diisopropyl ether for 5 hours to extract and remove the unsaponifiable substance.

The alkaline solution in the liquid extraction apparatus was taken out and filtered after sulfuric acid was added to make the solution strongly acidic, and then the acidic solution was refluxed with hexane for 5 hours to extract fatty acids.

The hexane extract of the fatty acids was washed with purified water until the extract became neutral (methyl orange), filtered, and concentrated to dryness, and then acetonitrile was added and the acetonitrile solution was left for 10 minutes after dissolution to precipitate acetonitrile insoluble substances.

After passing the supernatant of the acetonitrile solution through a Florisil (registered trademark) (activation completed for 3 hours at 130° C.) column, the column was washed with acetonitrile. The eluted acetonitrile was condensed under reduced pressure and dried to obtain the earthworm lipids.

(3) Purification of the Earthworm Lipid—Removal of highly unsaturated fatty acids—

Wakosil (registered trademark) C-300 (activation completed for 3 hours at 110° C.) was slurried with hexane and packed in a glass column (inner diameter: 15 mm, length: 30 cm), and Florisil (registered trademark) PR (activation completed for 3 hours at 130° C.) was slurried with hexane and laminated on top of the Wakosil (registered trademark) C-300. Anhydrous sodium sulfate was further laminated to obtain a column for fatty acid purification. The condensed and dried fatty acids were dissolved in hexane, loaded onto a column, and eluted with ether/hexane.

Example 2: Investigation of the Improvement Effect of Earthworm Lipid on Indigenous Bacterial Flora in the Skin (1) Experimental Method In a total of twelve subjects, nine persons who had atopic dermatitis and three healthy persons as shown in Table 2, control/squalane and 1% earthworm lipids/squalane prepared in Example 1 (direct saponification method) were applied to the inside of the left and right elbows of each subject by dropwise application of one drop each, with the same preparation applied on the same side twice a day, in the morning and evening (after bathing), with no knowledge of which preparation was added with the earthworm lipids to avoid the placebo effect. Application was performed for four weeks in three healthy persons and one person who had atopic dermatitis, and for two weeks in the other eight persons who had atopic dermatitis. The sample application site was scraped with a swab of swab kit for metagenome analysis to sample the microorganism on the skin. Bacterial 16srRNA genes were extracted from the swabbed swab and the sequences of the genes were read to compare with reference total bacterial sequence databases (approximately 15,000 species) for identifying bacterial species at species levels, and the population size, as well as Simpson's Index and Shannon Entropy, were calculated based on the number of DNA fragments of each bacterial species.

TABLE 2

| ID | Atopy History | Age | Sex | Period (weeks) |
|---|---|---|---|---|
| A-101 | Yes | 51 | man | 4 |
| A-102 | Yes | 25 | man | 2 |
| A-103 | Yes | 34 | man | 2 |
| A-104 | Yes | 38 | man | 2 |
| A-105 | Yes | 27 | man | 2 |
| A-106 | Yes | 26 | woman | 2 |
| A-107 | Yes | 30 | woman | 2 |
| A-108 | Yes | 29 | woman | 2 |
| A-109 | Yes | 45 | woman | 2 |
| B-101 | No | 53 | man | 4 |

TABLE 2-continued

| ID | Atopy History | Age | Sex | Period (weeks) |
|---|---|---|---|---|
| B-102 | No | 30 | man | 4 |
| B-103 | No | 35 | woman | 4 |

Moreover, for sebum after the completion of application for two weeks, sampling was performed at the sample application sites (both left and right sides) using an oil removing paper. The extraction, purification, and derivatization treatment of the sample were performed to perform GC/MS spectrometry, and the amount of sebum secretion was examined, and the ratio of the monoenoic acid having 16 carbon atoms (C16:1), which is considered to have highly antibacterial activity, to the linear saturated acid having 16 carbon atoms (C16:0) was analyzed.

(2) Analytical Results of the Subject A-109

Four subjects of the nine subjects who had atopic dermatitis had an extremely low amount of sebum secretion, one of which was A-109. In A-109, in addition to the change in the diversity, the replacement of bacterial species with higher occupancy was observed in comparison between before the application and 15th day of the application. The results of number of bacterial species on day 0, day 8, and day 15 of the application are shown in Table 3. The number of bacterial species with a flora occupation rate of 0.05% or more is counted.

As shown in Table 3, the application of the earthworm lipids resulted in a marked increase in the number of bacterial species compared to the control.

TABLE 3

| A-109, who has atopy history, | | Elapsed Day | | |
|---|---|---|---|---|
| 45 years old, woman | | Day 0 | Day 8 | Day 15 |
| The number of bacterial species | Earthworm lipids/Squalane | 127 | 180 | 162 |
| | Control/Squalane | 120 | 132 | 129 |

For A-109, the diversity analysis was performed by calculating Simpson's Index (the diversity is higher as it approaches 1) and Shannon Entropy (the diversity is higher as the numerical value is higher). The results are shown in FIG. 2.

Figure 2:
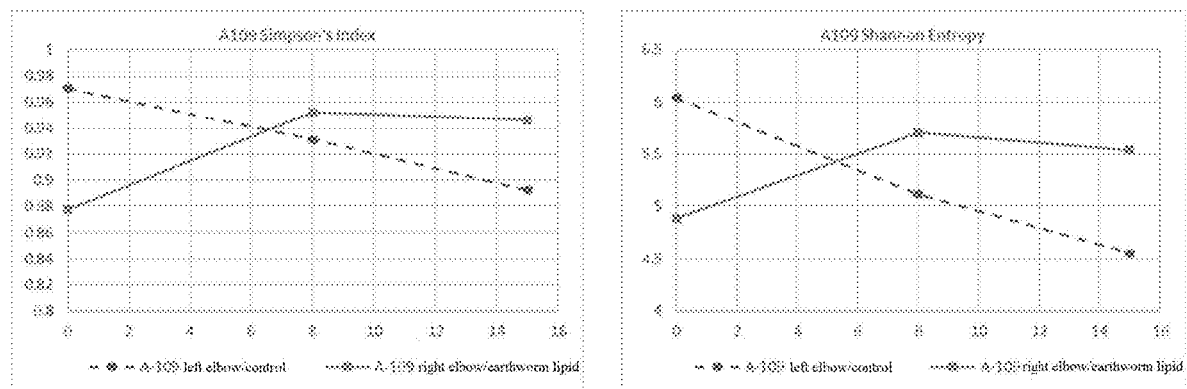
FIG. 2 represents the results of diversity analysis. The left-hand diagram shows the results of Simpson's Index analysis, and the right-hand diagram shows the results of Shannon Entropy analysis. The line types indicate the changes in the control and the changes in the case where earthworm lipids were applied, respectively.

As shown in FIG. 2, the diversity tended to decrease in A-109 control. On the other hand, the diversity showed a tendency to increase with the application of the earthworm lipids.

Figure 3:
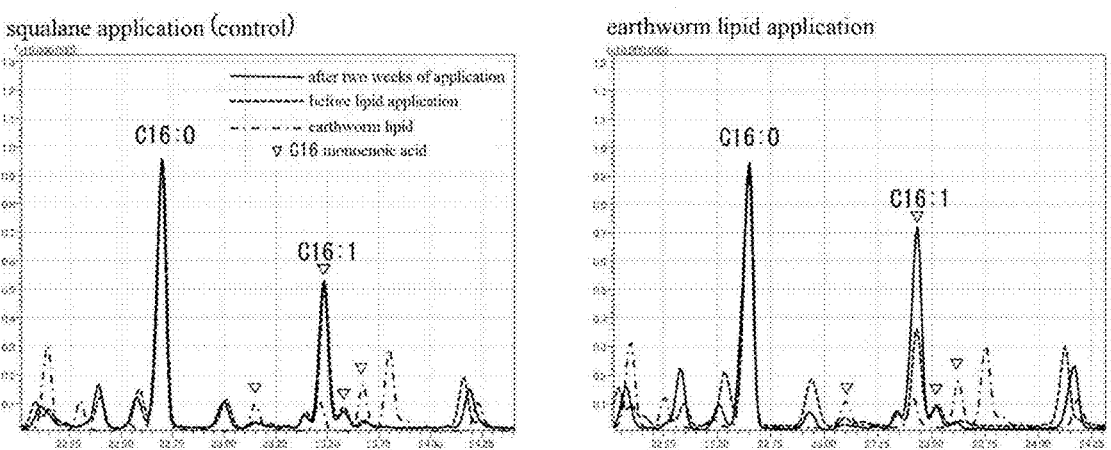
FIG. 3 represents chromatograms (TICs) showing the results of GC/MS analyses. The left and right figures, respectively, show the results of the control, and the results of the case where earthworm lipids were applied. The line types indicate the chromatograms of sebum after earthworm lipids were applied for 2 weeks, sebum before earthworm lipids are applied, and earthworm lipids, respectively, and ∇ indicates the peak of monoene fatty acid having 16 carbon atoms.

Moreover, the result shown in FIG. 3 was obtained by GC/MS spectrometry of sebum separately sampled. Note that in FIG. 3 the comparison is made by adjusting chromatographic scale with C16:0 (saturated fatty acid having 16 carbon atoms).

As shown in FIG. 3, the ratio of the monoenoic acid having 16 carbon atoms, which is considered to have high antibacterial activity, to the straight-chain saturated acid having 16 carbon atoms, did not change in the control as compared with that before the earthworm lipid application, but increased remarkably when the earthworm lipids were applied. The isomer different from the monoenoic acid contained in the applied earthworm lipids is increased, and thus it is presumed that the monoenoic acid isomer having 16 carbon atoms is produced from the earthworm lipids by the action of indigenous bacteria in the skin.

(3) Analytical Results of Subject A-107

Likewise, the subject A-107 was a person who had a less amount of sebum secretion, and the diversity of bacterial flora before the experiment was low.

The application of earthworm lipids increased the diversity of the bacterial flora and resulted in a replacement of the dominant bacterial species in both the control and the earthworm lipid application. The results of number of bacterial species are shown in Table 4.

As shown in Table 4, the application of earthworm lipids resulted in a marked increase in the number of bacterial species compared to the control.

TABLE 4

| A-107, who has atopy history, 30 years old, woman | | Elapsed Day | | |
|---|---|---|---|---|
| | | Day 0 | Day 8 | Day 15 |
| The number of bacterial species | Earthworm lipids/ Squalane | 51 | 100 | 102 |
| | Control/Squalane | 89 | 56 | 61 |

Figure 4:
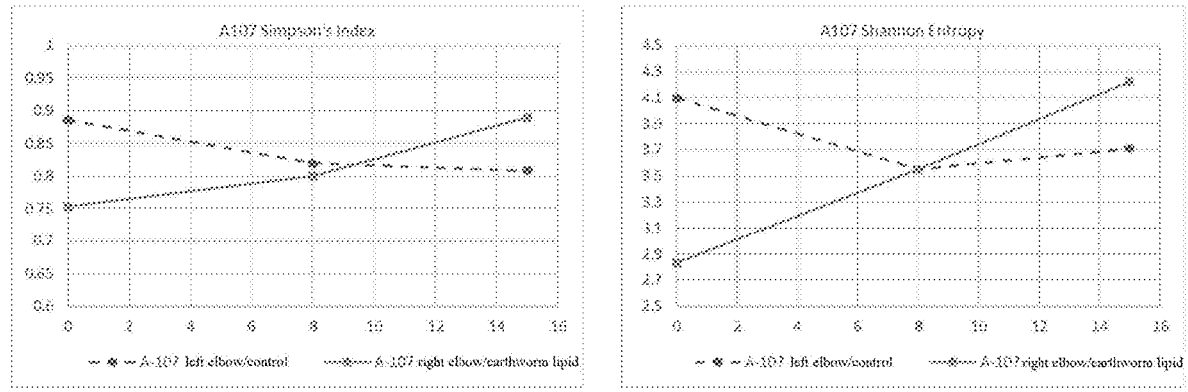
FIG. 4 represents the results of diversity analysis. The left-hand diagram shows the results of Simpson's Index analysis, and the right-hand diagram shows the results of Shannon Entropy analysis. The line types indicate the changes in the control and the changes in the case where earthworm lipids were applied, respectively.

For A-107 as well, the diversity analysis was also performed by calculating Simpson's Index and Shannon Entropy, and the results shown in FIG. 4 were obtained. As shown in FIG. 4, the diversity of control in A-107 tended to decrease, although the changes are small. On the other hand, the application of the earthworm lipids increased the diversity.

Figure 5:
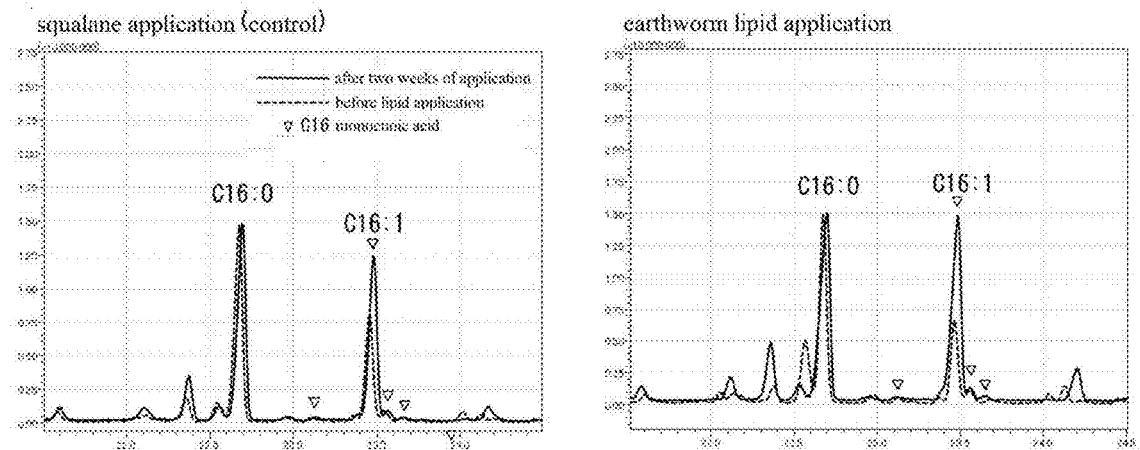
FIG. 5 represents chromatograms (TICs) showing the results of GC/MS analyses. The left and right figures, respectively, show the results of the control, and the results of the case where earthworm lipids were applied. The line types indicate the chromatograms of sebum after earthworm lipids were applied for 2 weeks, sebum before earthworm lipids are applied, and earthworm lipids, respectively, and ∇ indicates the peak of monoene fatty acid having 16 carbon atoms.

Likewise, the result shown in FIG. 5 was obtained by GC/MS spectrometry of sebum separately sampled. Note that in FIG. 5 as well, the comparison is made by adjusting the chromatographic scale with C16:0 (saturated fatty acid having 16 carbon atoms).

In A-107, while the ratio of monoenoic acid having 16 carbon atoms, which is considered to have highly antibacterial activity, to straight chain saturated acid having 16 carbon atoms was increased as compared with the pre-application, in both the control and the earthworm lipid application, probably due to the replacement of bacterial species, the increase rate of monoenoic acid was higher in the application of the earthworm lipids.

(4) Analytical Results of Subject A-105

The subject A-105 is a person who had a normal amount of sebum secretion and a high diversity of bacterial flora before application. The application reduced the rate of acne bacteria, which had a high occupancy rate, and the diversity was further increased accordingly. Both the control and the earthworm lipid application showed a replacement of bacterial species with higher occupancy. The results of number of bacterial species are shown in Table 5.

As shown in Table 5, in the case that sebum secretion was normal, the number of bacterial species only slightly increased even when the earthworm lipids were applied, but a clear decrease in the number of bacterial species was observed in the control.

TABLE 5

| A-105, who has atopy history, 27 years old, man | | Elapsed Day | | |
|---|---|---|---|---|
| | | Day 0 | Day 8 | Day 15 |
| The number of bacterial species | Earthworm lipids/ Squalane | 226 | 249 | 249 |
| | Control/Squalane | 240 | 167 | 169 |

Figure 6:
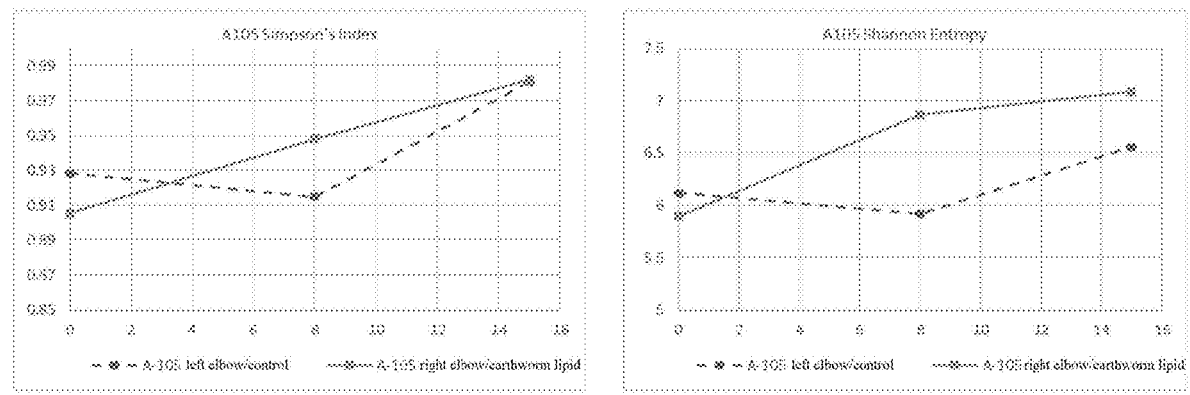
FIG. 6 represents the results of diversity analysis. The left-hand diagram shows the results of Simpson's Index analysis, and the right-hand diagram shows the results of Shannon Entropy analysis. The line types indicate the changes in the control and the changes in the case where earthworm lipids were applied, respectively.

For A-105 as well, the diversity analysis was also performed by calculating Simpson's Index and Shannon Entropy, and the results shown in FIG. 6 were obtained. As shown in FIG. 6, there was no significant difference in Simpson's Index between the control and the earthworm lipid application, but Shannon Entropy showed a higher diversity in the earthworm lipid application. It was presumed that this might be due to the large number of low-occupancy bacterial species.

Figure 7:
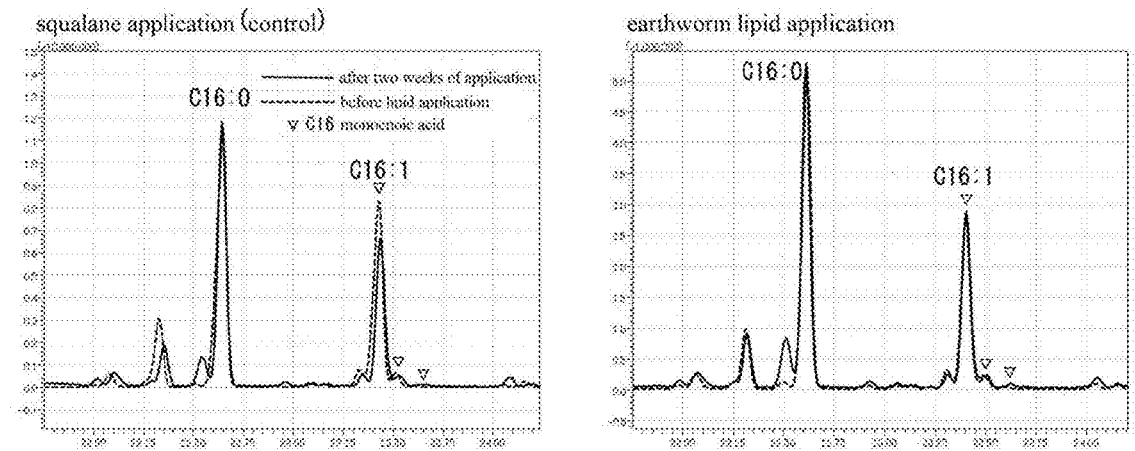
FIG. 7 represents chromatograms (TICs) showing the results of GC/MS analyses. The left and right figures, respectively, show the results of the control, and the results of the case where earthworm lipids were applied. The line types indicate the chromatograms of sebum after earthworm lipids were applied for 2 weeks, sebum before earthworm lipids are applied, and earthworm lipids, respectively, and ∇ indicates the peak of monoene fatty acid having 16 carbon atoms.

Likewise, the result shown in FIG. 7 was obtained by GC/MS spectrometry of sebum separately sampled. Note that in FIG. 7 as well, the comparison is made by adjusting the chromatographic scale with C16:0 (saturated fatty acid having 16 carbon atoms).

In A-105, the change of the monoenoic acid ratio by the application was hardly seen. The effect of the lipid application was presumed to be small in the person who naturally had a high diversity and a high sebum secretion.

INDUSTRIAL APPLICABILITY

The composition of the present invention is useful, for example, as a raw material for a skin care product or a cosmetic because it can enhance or improve the diversity of indigenous bacteria in the skin relative to the condition before application, thereby enhancing the barrier function of the skin and suppressing the proliferation of pathogenic bacteria. The composition of the present invention is also useful as a raw material of a pharmaceutical because the enhancement and improvement of the diversity of indigenous bacteria in the skin lead to the improvement and prevention of symptoms of atopic dermatitis and the retention of healthy skin.

The invention claimed is:

1. A composition used for controlling a degree of diversity of bacterial species in indigenous bacterial flora in the skin, comprising:
    an effective amount of earthworm lipids; and
    a base,
    wherein the earthworm is *Lumbricus rubellus*,
    the earthworm lipids are total lipids obtained by extracting and removing proteins from a raw earthworm to obtain an earthworm dehydrated cake, performing saponification of fatty acid esters in the earthworm dehydrated cake with an alkali, and extracting fatty acids as the earthworm lipids from the saponified product using a nonpolar organic solvent, and
    the base is at least one selected from the group consisting of white vaseline, yellow vaseline, cetanol, stearyl alcohol, stearic acid, hardened oil, gelled hydrocarbons, polyethylene glycol or macrogol, 1,3-butylene glycol, ethanol, isopropanol, liquid paraffin, and squalane.

2. The composition according to claim 1, which is directed for application to a subject with low sebum secretion or a subject with symptom of atopic dermatitis on the skin.

3. An enhancer of monoene fatty acid having 16 carbon atoms on the skin, comprising the composition according to claim 1.

4. The composition according to claim 1, wherein said composition is in a dosage form selected from the group consisting of an ointment, a cream, a gel, a liquid, a sheet, and an aerosol.

5. A cosmetic, comprising the composition according to claim 1.

6. A composition for controlling indigenous bacterial flora in the skin, which is obtained by extracting and removing proteins from a raw earthworm to obtain an earthworm dehydrated cake, performing saponification of fatty acid esters in the earthworm dehydrated cake with an alkali, and extracting fatty acids as the earthworm lipids from the saponified product using a nonpolar organic solvent,
wherein the earthworm is *Lumbricus rubellus*.

7. Earthworm lipids for controlling indigenous bacterial flora in the skin,
wherein the earthworm lipids are total lipids which are obtained by extracting and removing proteins from a raw earthworm to obtain an earthworm dehydrated cake, performing saponification of fatty acid esters in the earthworm dehydrated cake with an alkali, and extracting fatty acids as the earthworm lipids from the saponified material using a nonpolar organic solvent, and
the earthworm is *Lumbricus rubellus*.

8. The composition for controlling indigenous bacterial flora in the skin according to claim 6, wherein the nonpolar organic solvent is a hydrocarbon-based organic solvent.

9. A method of producing a composition for controlling the diversity of bacterial species in indigenous bacterial flora in the skin, comprising a step of extracting total earthworm lipids from an earthworm and a step of mixing the earthworm lipids with a base,
wherein the composition comprises an effective amount of earthworm lipids and base,
wherein the earthworm is *Lumbricus rubellus*,
wherein the extracting comprises extracting and removing proteins from a raw earthworm to obtain an earthworm dehydrated cake, performing saponification of fatty acid esters in the earthworm dehydrated cake with an alkali, and extracting fatty acids as the total earthworm lipids from the saponified product using a nonpolar organic solvent, and
wherein the base is at least one selected from the group consisting of white vaseline, yellow vaseline, cetanol, stearyl alcohol, stearic acid, hardened oil, gelled hydrocarbons, polyethylene glycol or macrogol, 1,3-butylene glycol, ethanol, isopropanol, liquid paraffin, and squalane.

10. The enhancer of monoene fatty acid having 16 carbon atoms on the skin according to claim 3, wherein said composition is in a dosage form selected from the group consisting of an ointment, a cream, a gel, a liquid, a sheet, and an aerosol.

11. A cosmetic, comprising the enhancer of monoene fatty acid having 16 carbon atoms on the skin according to claim 3.

12. The earthworm lipids for controlling indigenous bacterial flora in the skin according to claim 7, wherein the nonpolar organic solvent is a hydrocarbon-based organic solvent.

* * * * *